United States Patent
Holladay et al.

(10) Patent No.: US 6,505,936 B1
(45) Date of Patent: Jan. 14, 2003

(54) ELLIPSOIDAL CORNEAL MODELING FOR ESTIMATION AND RESHAPING

(75) Inventors: Jack T. Holladay, Bellaire, TX (US); Michael Smith, Orlando, FL (US); Travis Terry, Orlando, FL (US); Lance Marrou, Orlando, FL (US)

(73) Assignee: LaserSight Technologies, Inc., Winter Park, FL (US)

( * ) Notice: Subject to any disclaimer, the term of this patent is extended or adjusted under 35 U.S.C. 154(b) by 0 days.

(21) Appl. No.: 09/679,382

(22) Filed: Oct. 5, 2000

Related U.S. Application Data

(60) Provisional application No. 60/157,803, filed on Oct. 5, 1999, and provisional application No. 60/223,728, filed on Aug. 8, 2000.

(51) Int. Cl.⁷ .............................................. A61B 3/10
(52) U.S. Cl. ...................................................... 351/212
(58) Field of Search ................................ 351/205, 206, 351/210, 211, 212, 221, 246, 247; 600/558

(56) References Cited

U.S. PATENT DOCUMENTS

| | | |
|---|---|---|
| 4,050,192 A | 9/1977 | Volk |
| 4,420,228 A | 12/1983 | Humphrey |
| 4,660,946 A * | 4/1987 | Nakamura et al. .......... 351/212 |
| 4,710,193 A | 12/1987 | Volk |
| 4,732,148 A | 3/1988 | L'Esperance |
| 5,110,200 A | 5/1992 | Snook |
| 5,325,134 A * | 6/1994 | Kohayakawa ............... 351/212 |
| 5,350,374 A | 9/1994 | Smith |
| 5,411,501 A | 5/1995 | Klopotek |
| 5,549,597 A | 8/1996 | Shimmick et al. |
| 5,640,962 A | 6/1997 | Jean et al. |
| 5,644,396 A | 7/1997 | Hopkins, II |
| 5,695,509 A | 12/1997 | El Hage |
| 5,735,283 A | 4/1998 | Snook |
| 5,740,815 A | 4/1998 | Alpins |
| 5,749,867 A | 5/1998 | Alpins |
| 5,807,381 A | 9/1998 | Lieberman |
| 5,841,511 A | 11/1998 | D'Souza et al. |
| 5,861,955 A | 1/1999 | Gordon |
| 5,886,767 A * | 3/1999 | Snook ......................... 351/212 |
| 5,997,529 A | 12/1999 | Tang et al. |
| 6,033,396 A | 3/2000 | Huang et al. |
| 6,045,578 A | 4/2000 | Collins et al. |
| 6,080,144 A | 6/2000 | O'Donnell, Jr. |
| 6,082,856 A | 7/2000 | Dunn et al. |

FOREIGN PATENT DOCUMENTS

| | | |
|---|---|---|
| EP | 0 628 298 A1 | 12/1994 |
| WO | WO 9527452 | 10/1995 |

OTHER PUBLICATIONS

Achim Langenbucher et al., Ellipsoidal Fitting of Corneal Topography Data After Arcuate Keratomies with Compression Sutures, Ophthalmic Surgery and Lasers, Sep. 1998, pp. 738–748.

* cited by examiner

Primary Examiner—George Manuel
(74) Attorney, Agent, or Firm—William H. Bollman

(57) ABSTRACT

The present invention provides apparatus and techniques for performing prolate shaped corneal reshaping using an ellipsoid corneal modeler.

In accordance with the principles of the present invention, an ellipsoid corneal modeler is implemented with the well behaved conicoid, combined with a modeled surface which can be used for astigmatic treatments. An ellipsoid corneal modeler includes an ellipsoid fitter which utilizes two radii of curvature, asphericity (Q), and a surface rotation about the pupil center (roation of θ), yielding the equation:

$$\frac{x^2}{R_x} + \frac{y^2}{R_y} + \frac{z^z}{\left(\frac{2R_xR_y}{(1+Q)R_x+R_y}\right)} = \frac{2R_xR_y}{(1+Q)R_x+R_y} \quad (5)$$

Moreover, in accordance with the principles of the present invention, a target ellipsoid corneal surface with the applied refraction can be used to determine the required tissue removal for the given refractive change. This final shape will maintain the asphericity of the original corneal surface and therefore limit the spherical aberrations induced by the use of otherwise conventional techniques.

19 Claims, 5 Drawing Sheets

ELLIPSOIDAL CORNEAL MODELING FOR ESTIMATION AND RESHAPING

The present invention claims priority from U.S. Provisional Application No. 60/157,803 filed Oct. 5, 1999, entitled "Method and Apparatus for Using an Ellipsoidal Surface Shape for Corneal Reshaping" to Jack Holladay; and U.S. Provisional Application No. 60/223,728 filed Aug. 8, 2000 entitled "Custom Prolate Shape Corneal Reshaping" to Jack Holladay, the entirety of which are each expressly incorporated herein by reference.

BACKGROUND OF THE INVENTION

1. Field of the Invention

This invention relates to apparatus and methods to estimate refractive power of the human cornea, and to apparatus and methods to reshape the human cornea based on the estimation. More particularly, it relates to techniques to closely model the human cornea to accurately estimate the current refraction and determine a desired corneal shape.

2. Background of Related Art

Current refractive systems calculate estimates of the refractive power of the human cornea and reshape the human cornea based on these refractive errors. The devices that estimate the refractive power of the human cornea are known as corneal topographers. These devices normally use spherical models of the eye to report the refractive power of the cornea. The devices that reshape the human cornea are known as photo polishing systems. An exemplary system is the LaserSight LSX laser system. This device uses a small beam (nominal 1 mm) and a relatively high repetition rate (100 Hz or greater) to remove tissue from the human cornea and reshape it as desired. The combination of the small spot size and x-y scanning controls allows for fine control of the corneal tissue removed.

Both topography systems and photo polishing systems require a model of the human cornea to determine the current refractive power of a patient's cornea, and/or to determine a target ablated corneal surface. The current techniques for estimation of corneal shape use spherical, toric, meridional variation, or conicoid models of the cornea. Depending on which model is chosen, differing estimations of corneal refraction can be obtained.

The first model used for the human cornea was a sphere. Work by Charles R. Munnerlyn, Ph.D in "Protorefractive keratectomy: A technique for laser refractive surgery", Journal Cataract and Refractive Surgery, vol. 14, Jan. (1988), shows that if the initial shape of the human cornea could be modeled as a sphere, then the tissue to remove to target the ideal refractive shape is the intersection with a different sphere that is determined by the refraction. The technique to determine this second sphere is a direct consequence of Snell's law of refraction and the measured corneal index of refraction. When using this model to determine the material to remove for the desired corneal refractive power, the difference between this model and the real shape of the human cornea can create known errors such as induced spherical aberration. Additionally, this technique is only applicable to treatments that are of constant refractive correction across the entire surface because it is radially symmetric. This model is not appropriate for people with any type of astigmatism.

The second technique used to model the cornea is based on a torus. A torus will compensate for the spherical models limitations. With this model, curvatures along a major and minor axis which are constant along their respective axes can be estimated. Current contact and eyeglass technology uses toric lenses. This model can be used for topographic estimation of the refractive power of the human cornea or as a basis for planning tissue removal to go from an initial to a final refractive power of a cornea.

However, a known problem with this technique is that the fit does not account for spherical aberration. Moreover, terms or parameters which are required to specify such a torus are radius of curvature along the major and minor axes and the rotation E for alignment of the axis.

To address the issue of human corneal modeling while accounting for spherical aberrations, the use of meridional variation and conicoid surfaces were explored. For instance, a paper by Kiely (i.e., Kiely, P.M. "The mean shape of the human cornea". Optica Acta, 1982, Vol. 29, No. 8, pp 1024–1040) demonstrates the usefulness of aspheric corneal shapes. The conicoid presented by Kiely may be described best as a prolate or oblate spheroid. This class of shapes are spheres that have been either flattened or stretched along a single axis.

Kiely further disclosed that the nominal stretching of the human cornea uses a Q parameter of −0.26 (±0.18). This fitting model requires a further parameter over the basic spherical corneal model that includes a Q value.

A typical equation that models a conicoid was described, e.g., by George Smith in "Construction, Specification, and Mathematical Description of Aspheric Surfaces", American Journal of Optometry and Physiological Optics, vol. 60, No. 3, pp. 216–223 (1983). Such a conicoid equation can be written as:

$$x^2+y^2+(1+Q)z^2-2zR=0 \quad (1)$$

Equation (1) is a good model for the human corneas, but generally only so long as the cornea is rotationally symmetric about the pupil or optical axis of the eye. However, this model does not fit well for people with corneal astigmatism, a very common ailment among corneal reshaping patient's.

To account for corneal astigmatism, Kiely proposed the use of a meridional variation surface. This surface is generated by defining a minor and major axis angle and refractive power, and parametrically determining all other values as a function of these parameters by the following equations:

$$Q(\theta)=Q_1+Q_2\cos^2(\theta-\alpha) \quad (2)$$

$$R(\theta)=R_1+R_2\cos^2(\theta-\alpha) \quad (3)$$

In equations (2) and (3), $Q_1$, $Q_2$, and $R_1$, $R_2$ are the major and minor axis Q values, and radii of curvature (refractive power along the axis), respectively. The values of $\alpha$ and $\beta$ specify the angles containing the maximum and minimum value of Q and R, respectively.

The conicoid does provide a reasonable result, but generally only when used as a basis for removing tissue that does not introduce artifacts. Artifacts relate to the recognition that the difference between two conicoids is continuous, whereas the difference between two meridional variable surfaces is not. However, it does not allow for astigmatic treatment types. The meridional variation surface closely models the astigmatic corneal surface, but using it as a basis for tissue removal introduces artifacts that are based upon the properties of this surface type.

There is thus a need for an ablation laser system and method which utilizes accurate ellipsoidal modeling for precise and realistic refractive correction of corneas.

SUMMARY OF THE INVENTION

In accordance with one aspect of the present invention, a corneal surface estimation modeler comprises a corneal measurement input module to receive corneal measurement information regarding a patient's cornea, and an ellipsoid fitter to generate a best fit ellipsoid to the corneal measurement information relating to a corneal surface of the patient's cornea.

A method of ablating corneal tissue in accordance with another aspect of the present invention comprises modeling a patient's cornea with a best-fit ellipsoid, comparing the best-fit ellipsoid with an ideal ellipsoid, and determining a difference between the best-fit ellipsoid and an ideal ellipsoid.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

The present invention provides apparatus and techniques for performing prolate shaped corneal reshaping using an ellipsoid corneal modeler.

In accordance with the principles of the present invention, an ellipsoid corneal modeler is implemented with the well behaved conicoid, combined with a modeled surface which can be used for astigmatic treatments.

In accordance with the present invention, an ellipsoid corneal modeler utilizes a form of a general ellipsoid formula. In particular, a general ellipsoid formula may be expressed as in the following equation (4):

$$\frac{x^2}{a^2} + \frac{y^2}{b^2} + \frac{z^2}{c^2} = 1 \tag{4}$$

In accordance with the techniques and apparatus of the present invention, estimation and reshaping modules are implemented to perform the functions of equation (4).

In particular, to adapt equation (4) to the needs of corneal reshaping, the following parameters are implemented: two radii of curvature, asphericity (Q), and a surface rotation about the pupil center (roation of θ), yielding the following equation:

$$\frac{x^2}{R_x} + \frac{y^2}{R_y} + \frac{z^2}{\left(\frac{2R_xR_y}{(1+Q)R_x+R_y}\right)} = \frac{2R_xR_y}{(1+Q)R_x+R_y} \tag{5}$$

In Equation (5), the z-axis is defined as being normal to center of the cornea and projecting back through the patient's pupil. This equation (5), and a rotation of the final equation by an angle θ about the z-axis, defines the basis of this invention for refractive surface estimation and surgical treatment planning.

Equation (5) is implemented in a suitable corneal modeler of a surgical planning tool, e.g., in an ablation pattern determination module of a LaserSight LSX laser system.

To implement Equation (5) in a suitable corneal modeler, the initial refractive power of a cornea may be determined using a numerical best fit scheme, and by using an empirically determined refraction (e.g., through the use of an auto-refractor, phoropter, wavefront, or other refractive measurement device).

Moreover, in accordance with the principles of the present invention, a target ellipsoid corneal surface with the applied refraction can be used to determine the required tissue removal for the given refractive change. This final shape will maintain the asphericity of the original corneal surface and therefore limit the spherical aberrations induced by the use of other techniques.

Figure 1:
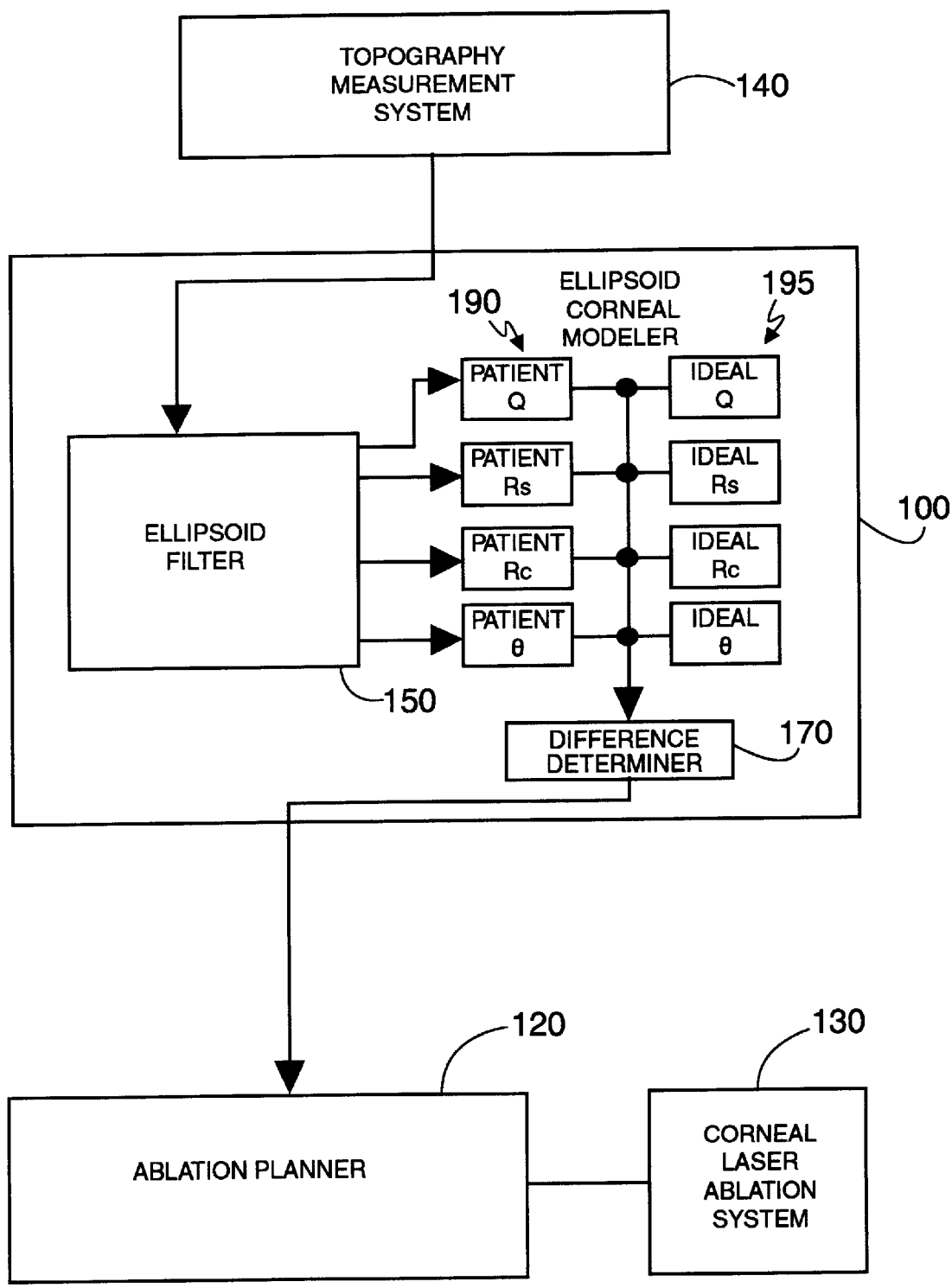
FIG. 1 shows an exemplary ellipsoidal corneal modeler, in accordance with the principles of the present invention.

FIG. 1 shows an exemplary ellipsoidal corneal modeler 100, in accordance with the principles of the present invention.

In particular, as shown in FIG. 1, an ellipsoidal corneal modeler 100 is implemented in conjunction with an ablation planner 120, which in turn determines a desired ablation pattern for use by a suitable corneal laser ablation system 130, e.g., a LaserSight LSX laser system.

The ellipsoidal corneal modeler 100 receives patient topography information, which is input to an ellipsoid fitter 150 implementing Equation (5). The ellipsoid fitter 150 determines a best-fit ellipsoid based on an ellipsoid as defined in Equation (5), and outputs patient ellipsoid parameters 190, e.g., Q, $R_s$, $R_c$, and θ. These patient ellipsoid best-fit parameters 190 are compared to ideal or target ellipsoid parameters 195, and a difference between the two ellipsoids (actual patient ellipsoid and ideal or target ellipsoid) is determined by a suitable difference determiner 170.

The difference information provided by the difference determiner 170 forms the basis in the creation of a target corneal refractive surface through the use of a patient-specific ablation pattern to be generated by an ablation planner 120. The difference between the initial patient topography and the target surface or the initial estimated ellipsoid and the target. refractive surface defines the material to be removed. This difference map can then be exported to a laser system for application to the cornea. For instance, an ablation in accordance with an ablation pattern derived by the ablation planner 120 may be performed or utilized, e.g., by the corneal laser ablation system 130.

Figure 2:
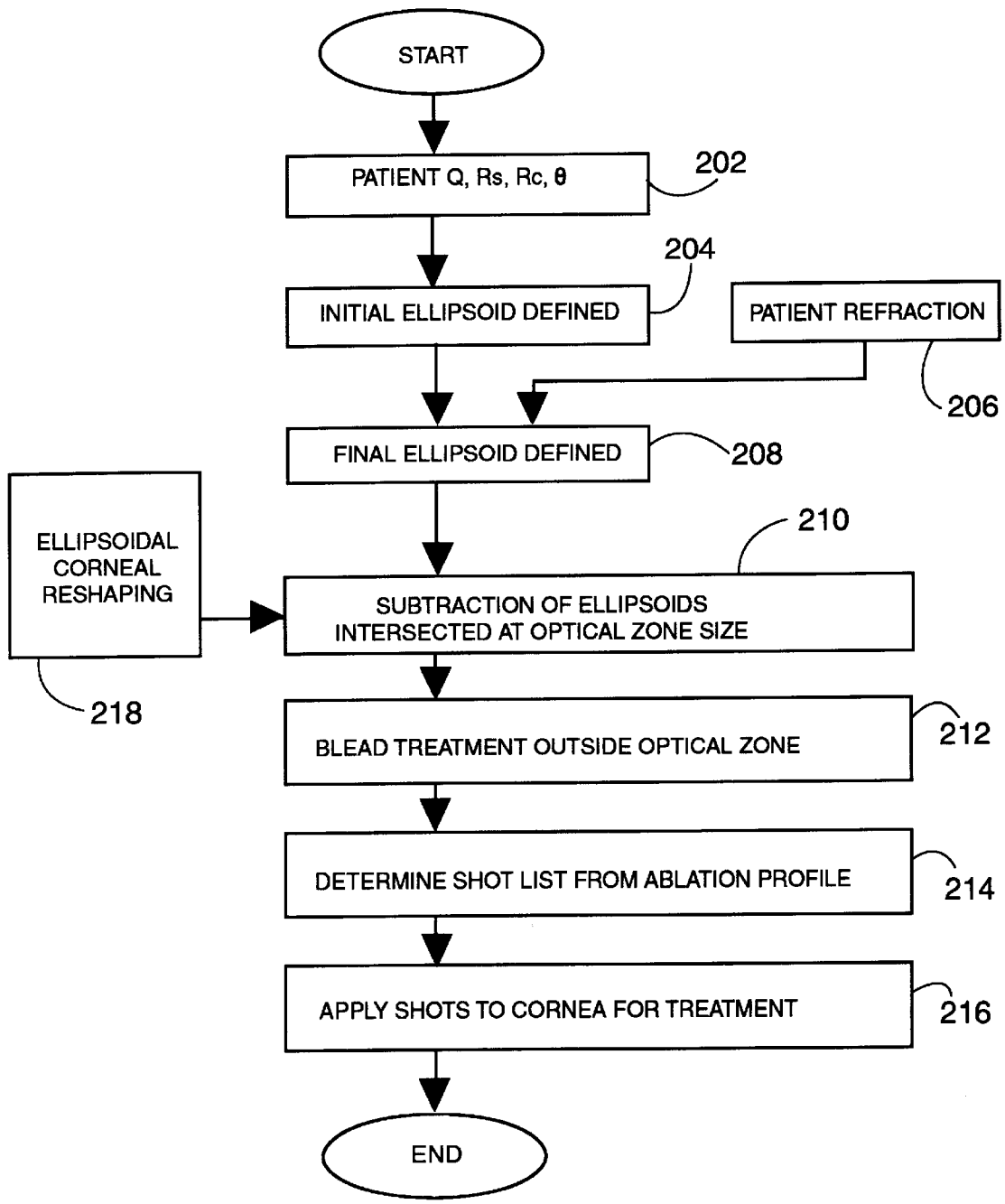
FIG. 2 shows an exemplary process of ellipsoidal corneal modeling in a corneal laser ablation system, in accordance with the principles of the present invention.

FIG. 2 shows a process of ellipsoidal corneal modeling in a corneal laser ablation system, in accordance with the principles of the present invention.

In particular, steps 202–218 show an exemplary process of modeling a corneal with an ellipsoid corneal modeler 100.

Figure 3:
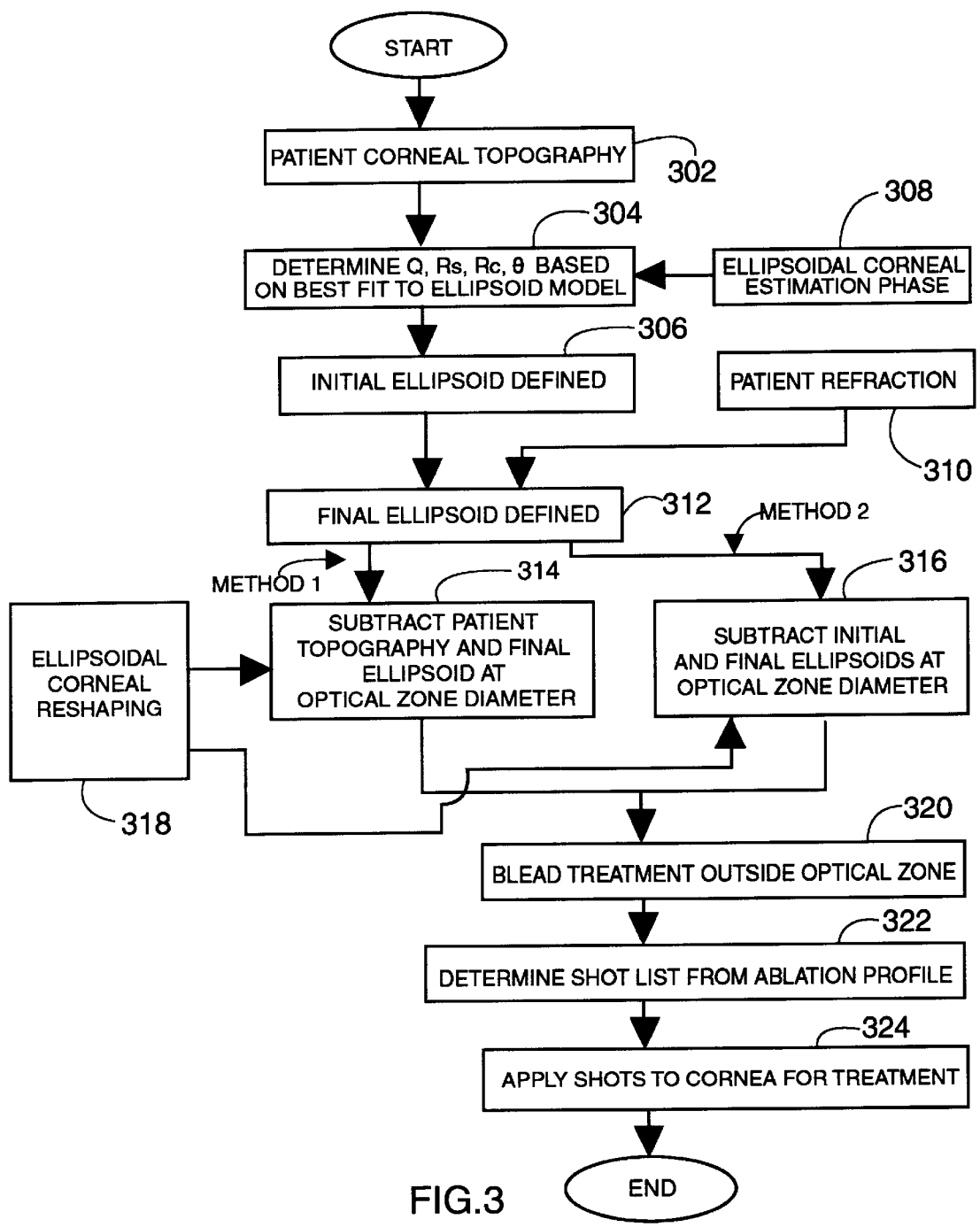
FIG. 3 shows an exemplary process of ellipsoidal corneal modeling together with the use of corneal topography measurement of a patient's cornea to control a corneal laser ablation system, in accordance with the principles of the present invention.

FIG. 3 shows an exemplary process of ellipsoidal corneal modeling together with the use of corneal topography measurement of a patient's cornea to control a corneal laser ablation system, in accordance with the principles of the present invention.

In particular, steps 302–324 depict the functions including an ellipsoid corneal modeler 100 in accordance with the principles of the present invention can also or alternatively be used in conjunction with corneal topography (i.e., customized ablation) and/or in conjunction with eye refractive power estimation technology, to target a final ellipsoidal shape that satisfies and accomplishes the desired refractive power correction, as well as limits spherical aberrations.

Additionally, ellipsoidal corneal surface fitting in accordance with the principles of the present invention can accommodate additional parameters. For instance, the -modeled ellipsoid shape can include additional parameters for tilt (i.e., rotation about the x-axis and/or rotation about the y-axis) that would bring the modeled ellipsoid in line with the optical axis instead of the visual axis.

Figure 4:
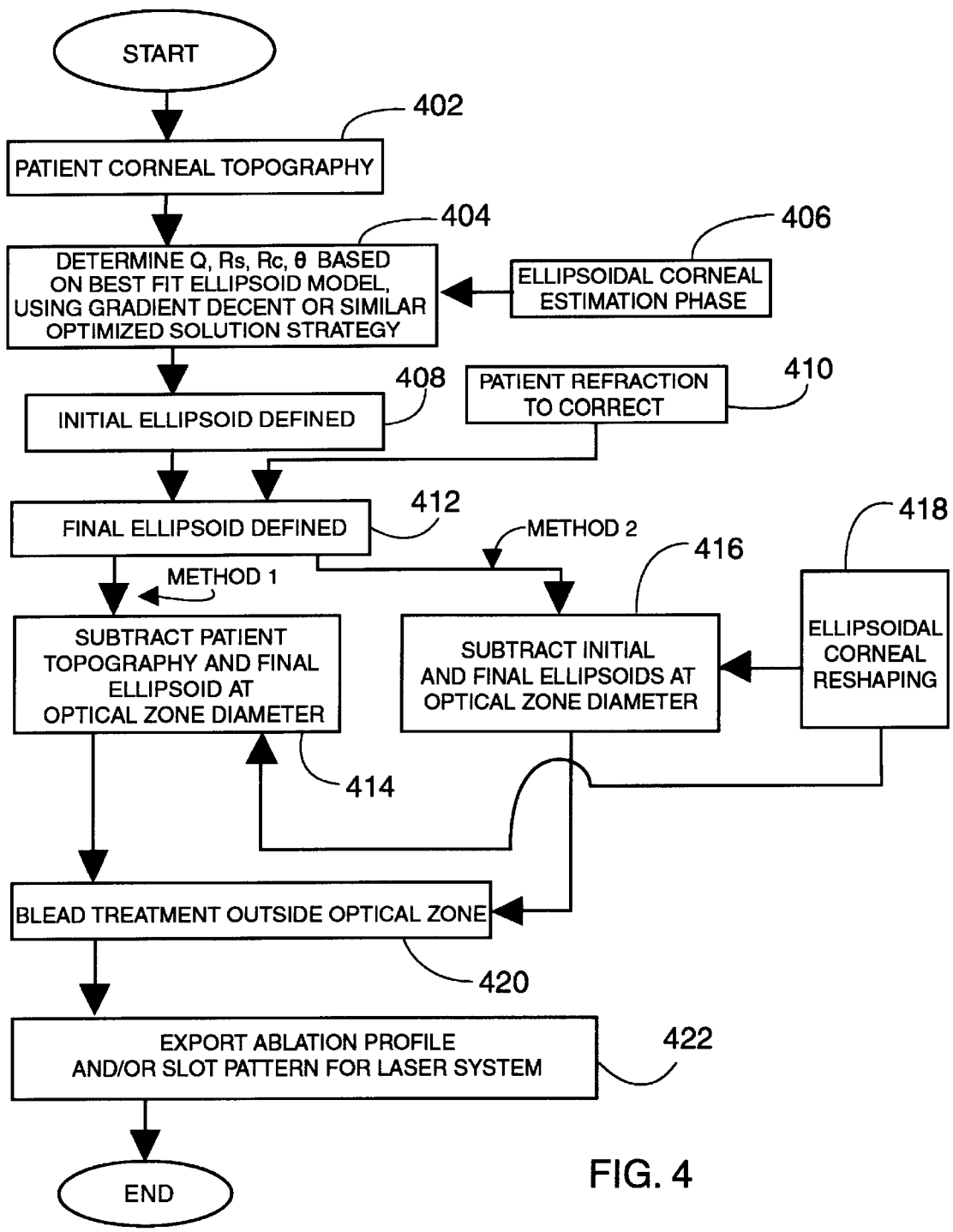
FIG. 4 shows an exemplary process of ellipsoidal corneal estimation modeling in an ablation planning system, in accordance with the principles of the present invention.

FIG. 4 shows an exemplary process of ellipsoidal corneal estimation modeling in an ablation planning system, in accordance with the principles of the present invention.

In particular, as shown in steps 402–422 of FIG. 4, an ellipsoidal corneal modeler in accordance with the principles of the present invention may be implemented in, e.g., a photo polishing laser system, a corneal topography system, and/or an ablation planning system. Of course, an ellipsoidal corneal modeler apparatus and techniques in accordance with the principles of the present invention may be implemented and/or utilized in different ways by various apparatus, within the scope of the present invention.

As an example, the ellipsoidal corneal modeler may be implemented in, e.g., a LaserSight LSX laser system to form the basis of a photo polishing laser system for planning ellipsoidal difference ablations.

Figure 5:
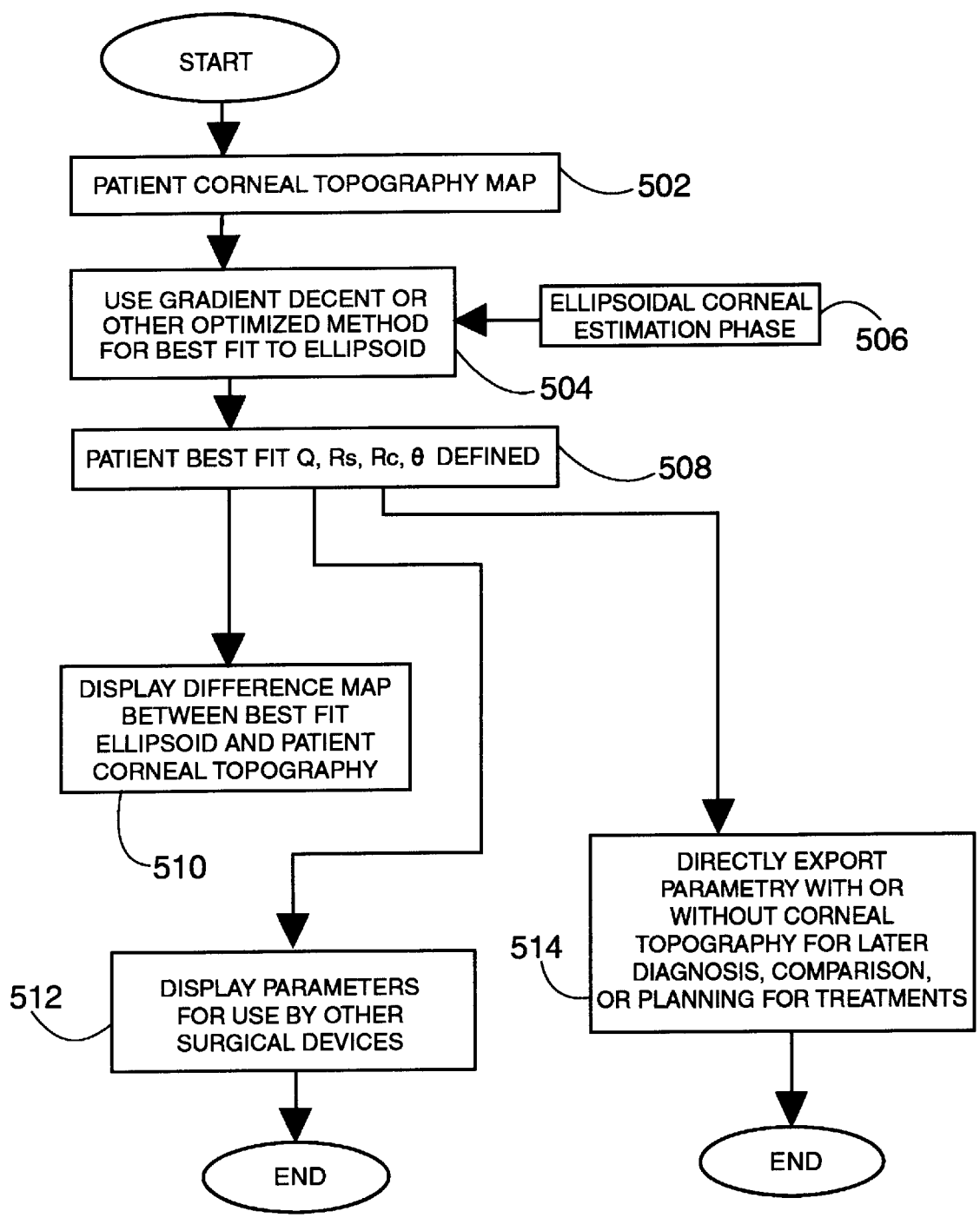
FIG. 5 shows an exemplary process of ellipsoidal corneal modeling in a corneal topography system, in accordance with the principles of the present invention.

FIG. 5 shows an exemplary process of ellipsoidal corneal modeling in a corneal topography system, in accordance with the principles of the present invention.

For instance, as shown in steps 502–514 of FIG. 5, a corneal laser ablation system may import corneal topography and/or refraction error information as input data to the ellipsoidal corneal modeler to allow customized ellipsoidal corneal modeling and ablation, to directly estimate a patient's actual corneal refraction, and/or in determining a desired final ellipsoidal corneal shape.

An ellipsoidal corneal modeler in accordance with the principles of the present invention may be implemented in, e.g., a corneal topography system. For example, a corneal topography system may utilize an ellipsoidal corneal modeler to determine an ideal ellipsoid fit for display or patient diagnosis.

In particular, a normal patient corneal shape is well estimated by an ellipsoid in accordance with the principles of the present invention. As such, a display of localized corneal errors can be determined by showing the difference between the input corneal topography data, and a best-fit ellipsoid from an ellipsoid corneal modeler in accordance with the principles of the present invention.

Additionally, ellipsoid parameters may be determined for use in customized ablations which require the estimation of corneal refraction and shaping characteristics. For instance, corneal surface data including corneal topography data can be exported, together with best-fit ellipsoid parameters, for use by other corneal measurement and/or reshaping devices.

An ellipsoidal corneal modeler in accordance with the principles of the present invention may also be implemented in an ablation planning system. Such an ablation planning system may be, e.g., a stand-alone device, or a device which is coupled to a corneal laser ablation system, to a corneal topography measurement system, or to any other corneal diagnostic or medical device that may be used to determine a pre- or post-operative surgery profile of a patient's corneal surface and/or to determine a shot pattern in accomplishing a given treatment.

While the invention has been described with reference to the exemplary embodiments thereof, those skilled in the art will be able to make various modifications to the described embodiments of the invention without departing from the true spirit and scope of the invention.

What is claimed is:

1. A corneal surface estimation modeler, comprising:
  a corneal measurement input module to receive corneal measurement information regarding a patient's cornea; and
  an ellipsoid fitter to generate a best fit ellipsoid to said corneal measurement information relating to a corneal surface of said patient's cornea.

2. The corneal surface estimation modeler in accordance with claim 1, further comprising:
  an ablation planner, receiving information relating to said best fit ellipsoid, to generate an ablation pattern for presentation to a corneal surface.

3. The corneal surface estimation modeler in accordance with claim 1, wherein:
  said corneal measurement information is corneal topographical data.

4. The corneal surface estimation modeler in accordance with claim 3, further comprising:
  a corneal topography measurement device to generate said corneal topographical data.

5. The corneal surface estimation modeler in accordance with claim 1, further comprising:
  an ablation planner to determine a desired amount of corneal tissue to remove based on said best-fit ellipsoid model of said patient's corneal surface.

6. The corneal surface estimation modeler in accordance with claim 1, wherein:
  said corneal measurement information is corneal refractive error measurement data.

7. A corneal surface estimation modeler, comprising:
  a corneal measurement input module to receive corneal measurement information regarding a patient's cornea; and
  an ellipsoid fitter to generate a best fit ellipsoid to said corneal measurement information relating to a corneal surface of said patient's cornea, said ellipsoid fitter implementing a best fit ellipsoid in accordance with the following equation:

$$\frac{x^2}{R_x} + \frac{y^2}{R_y} + \frac{z^z}{\left(\frac{2R_xR_y}{(1+Q)R_x+R_y}\right)} = \frac{2R_xR_y}{(1+Q)R_x+R_y}$$

wherein a z-axis is defined as being normal to a center of said patient's cornea and projecting back through said patient's pupil.

8. The corneal surface estimation modeler in accordance with claim 7, wherein:
  said ellipsoid fitter rotates an ellipsoid about said z-axis to determine said best-fit ellipsoid.

9. The corneal surface estimation modeler in accordance with claim 7, wherein:
said ellipsoid fitter rotates an ellipsoid about said z-axis to produce a desired target corneal surface shape and alignment for an astigmatic treatment.

10. The corneal surface estimation modeler in accordance with claim 7, wherein:
said best-fit ellipsoid is tilted to align with an optical axis of said patient's eye.

11. A corneal surface estimation modeler, comprising:
a corneal measurement input module to receive corneal refractive error measurement data regarding a patient's cornea, said corneal refractive error measurement data being in a form of at least one of:
wavefront Zernike polynomials, and
an error matrix; and
an ellipsoid fitter to generate a best fit ellipsoid to said corneal measurement information relating to a corneal surface of said patient's cornea.

12. A corneal surface estimation modeler, comprising:
a corneal measurement input module to receive corneal refractive error measurement data regarding a patient's cornea, said corneal refractive error measurement data being in a form of a sphere and cylinder having an axis; and
an ellipsoid fitter to generate a best fit ellipsoid to said corneal measurement information relating to a corneal surface of said patient's cornea.

13. A corneal surface estimation modeler, comprising:
a corneal measurement input module to receive corneal measurement information regarding a patient's cornea;
an ellipsoid fitter to generate a best fit ellipsoid to said corneal measurement information relating to a corneal surface of said patient's cornea; and
an ablation planner to determine an amount of corneal tissue to ablate based on an empirically derived transfer function to achieve a target ellipsoid corneal surface final shape after tissue removal.

14. The corneal surface estimation modeler in accordance with claim 13, wherein:
said ablation planner determines said empirically derived transfer function utilizing a corneal topography difference map.

15. The corneal surface estimation modeler in accordance with claim 13, wherein:
said ablation planner determines said empirically derived transfer function utilizing a refractive difference between a pre-operative best-fit ellipsoid and a post-operative best-fit ellipsoid, as compared to an expected treatment.

16. A method of ablating corneal tissue, comprising:
modeling a patient's cornea with a best-fit ellipsoid;
comparing said best-fit ellipsoid with an ideal ellipsoid; and
determining a difference between said best-fit ellipsoid and an ideal ellipsoid.

17. The method of ablating corneal tissue according to claim 16, further comprising:
exporting said difference to an ablation planner, for use in a determination of a corneal surface ablation pattern.

18. Apparatus for ablating corneal tissue, comprising:
means for modeling a patient's cornea with a best-fit ellipsoid;
means for comparing said best-fit ellipsoid with an ideal ellipsoid; and
means for determining a difference between said best-fit ellipsoid and an ideal ellipsoid.

19. The apparatus for ablating corneal tissue according to claim 18, further comprising:
means for exporting said difference to an ablation planner, for use in a determination of a corneal surface ablation pattern.

* * * * *